(12) United States Patent
Hodgkins et al.

(10) Patent No.: US 11,180,432 B1
(45) Date of Patent: Nov. 23, 2021

(54) PROCESS FOR FLUIDIZED CATALYTIC CRACKING OF DISULFIDE OIL TO PRODUCE BTX

(71) Applicant: SAUDI ARABIAN OIL COMPANY, Dhahran (SA)

(72) Inventors: Robert Peter Hodgkins, Dhahran (SA); Omer Refa Koseoglu, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 17/151,312

(22) Filed: Jan. 18, 2021

(51) Int. Cl.
C07C 4/06 (2006.01)
C07C 6/12 (2006.01)
C07C 7/00 (2006.01)
C07C 7/163 (2006.01)

(52) U.S. Cl.
CPC ............... *C07C 4/06* (2013.01); *C07C 6/126* (2013.01); *C07C 7/005* (2013.01); *C07C 7/163* (2013.01)

(58) Field of Classification Search
CPC ........... C07C 4/06; C07C 6/126; C07C 7/163; C07C 7/005; C10G 69/04; C10G 45/32; C10G 11/18; C10G 19/16
See application file for complete search history.

(56) References Cited

U.S. PATENT DOCUMENTS

| | | |
|---|---|---|
| 3,074,878 A | 1/1963 | Pappas |
| 4,419,221 A | 11/1983 | Yasuda et al. |
| 4,980,053 A | 12/1990 | Li et al. |
| 5,326,465 A | 7/1994 | Yongqing et al. |
| 5,462,652 A | 10/1995 | Wegerer |
| 5,685,972 A | 11/1997 | Timken et al. |
| 6,656,346 B2 | 12/2003 | Ino et al. |
| 8,617,384 B2 | 12/2013 | Haizmann et al. |
| 10,208,259 B2 | 2/2019 | Buchbinder et al. |
| 10,358,612 B2 | 7/2019 | Pelaez |
| 2015/0166435 A1 | 6/2015 | Serban et al. |
| 2018/0155642 A1 | 6/2018 | Al-Ghamdi et al. |
| 2020/0181506 A1 | 6/2020 | Koseoglu et al. |
| 2020/0181517 A1 | 6/2020 | Koseoglu et al. |
| 2020/0332201 A1 | 10/2020 | Koseoglu et al. |

FOREIGN PATENT DOCUMENTS

WO  WO 94/09090  *  4/1994

OTHER PUBLICATIONS

Y. Oh, et al., "Selective hydrotreating and hydrocracking of FCC light cycle oil into high-value light aromatic hydrocarbon," Appllied Catalysis A: General, 577:85-98 (May 5, 2019).
G. C. Laredo, et al., "Effect of the experimental conditions on BTX formation from hydrotreated light cycle oil," Applied Petrochemical Research, 10:21-34 (2020).

\* cited by examiner

*Primary Examiner* — Thuan D Dang
(74) *Attorney, Agent, or Firm* — Abelman, Frayne & Schwab

(57) ABSTRACT

Relatively low value disulfide oil (DSO) compounds produced as by-products of the mercaptan oxidation (MEROX) processing of refinery hydrocarbon streams, and oxidized disulfide oils (ODSO), are economically converted to value-added BTX by introducing the DSO and/or ODSO compounds as the feed to a fluidized catalytic cracking (FCC) unit and recovering the liquid products. The liquid FCC products are introduced as the feedstream to a selective naphtha hydrogenation and hydrotreating process for desulfurization and are then further separated in an aromatics extraction process for the recovery of BTX.

16 Claims, 8 Drawing Sheets

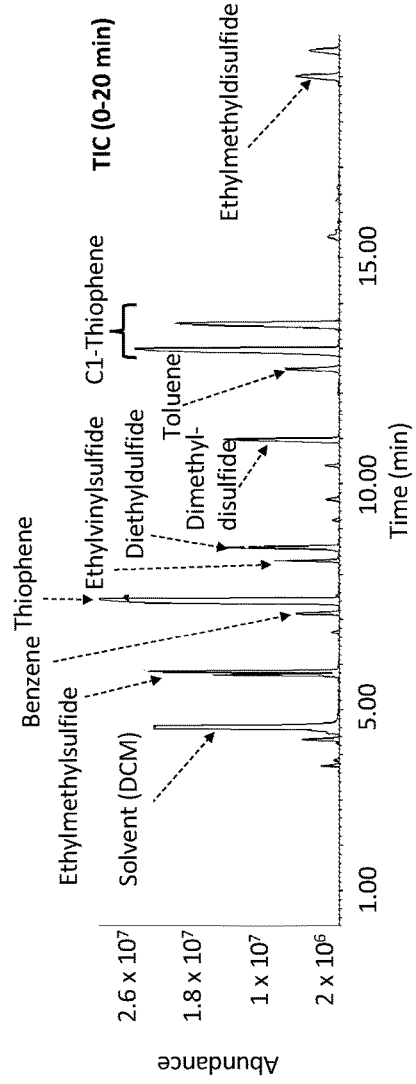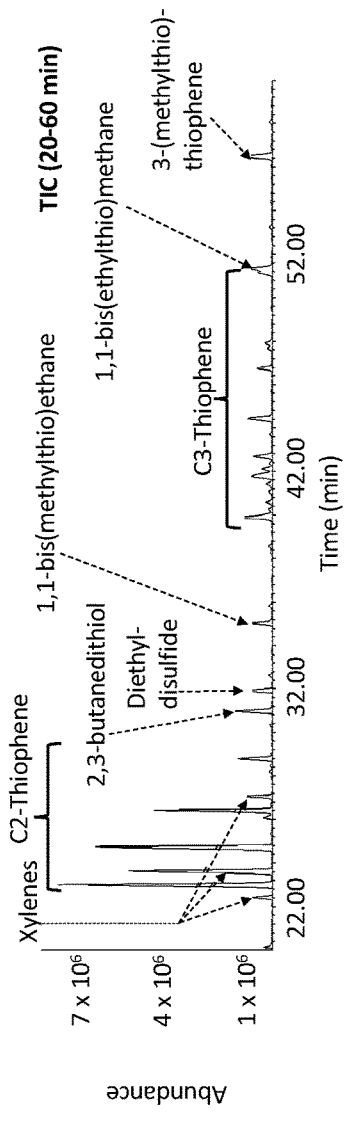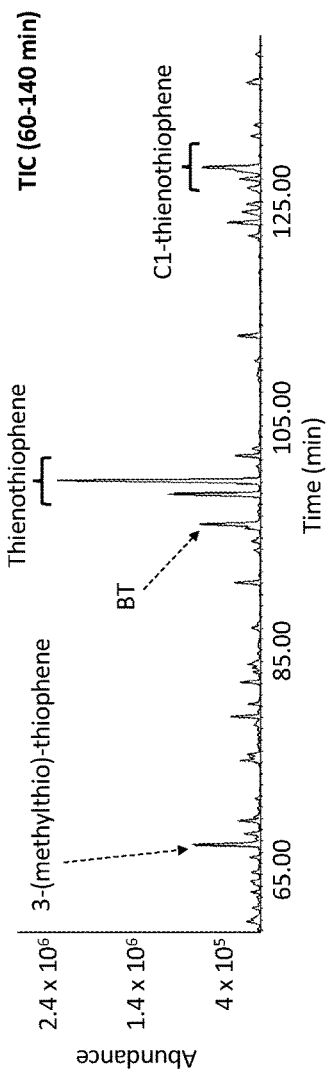
FIG. 8a
FIG. 8b
FIG. 8c

PROCESS FOR FLUIDIZED CATALYTIC CRACKING OF DISULFIDE OIL TO PRODUCE BTX

BACKGROUND OF THE INVENTION

Field of the Invention

This disclosure is directed to the processing of disulfide oil (DSO) compounds and their derivatives to produce BTX.

Description of Related Art

FCC Process

Fluidized catalytic cracking (FCC) is a ubiquitous and very important process in hydrocarbon refinery operations. The FCC process catalytically converts, or cracks, hydrocarbon feedstocks boiling in the vacuum gas oil range, i.e., 370° C. to 520° C., without the addition of hydrogen to the conversion zone, which is typically operated at temperatures in the range of from about 480° C. to about 650° C. using a circulating stream of regenerated catalyst.

Fluidized catalytic cracking (FCC) process catalytically cracks the petroleum-derived hydrocarbons boiling in vacuum gas oil range with an acidic catalyst maintained in a fluidized state that is regenerated on a continuous basis. The principal product from the FCC process has generally been gasoline. Other products produced in smaller quantities via FCC processes include light hydrocarbons gases, C1-C4, and unconverted cycle oils. Coke deposited on the catalyst in the process is burned off in a fluidized regenerator at high temperatures and in the presence of air prior to recycling the hot regenerated catalyst to the reaction zone.

The FCC process has the advantages of being performed without the addition of hydrogen and at relatively low operating pressure, i.e., 3 to 4 bars. However, the process requires relatively high reaction temperatures which accelerate conversion of some of the hydrocarbons to coke thereby decreasing the potentially greater volumetric yield of the normally liquid hydrocarbon product. This coke forms on the catalyst, and the FCC process requires the continuous regeneration of the catalyst by burning off the coke prior to the recycling of the catalyst. In recent years, in addition to the production of gasoline by FCC operations, there has been a growing interest in increasing the production of light olefins such a propylene. The light olefins are valuable raw materials for various chemical processes and provide significant economic advantages to refiners, particularly with respect to oil refineries that are highly integrated with petrochemical production facilities.

There are different methods for producing light olefins by the FCC process. Some FCC operating conditions are based on a short contact time of the feedstock with the catalyst, e.g., as is disclosed in U.S. Pat. Nos. 4,419,221, 3,074,878, and 5,462,652. However, the short contact time between feedstock and catalyst typically results in a relatively low conversion of the feed.

Other FCC processes are based on using a catalyst additive such as pentasil-type zeolite, for instance, as is disclosed in U.S. Pat. No. 5,326,465. However, the use of a pentasil-type zeolite catalyst has the disadvantage of enhancing the yield of light fraction hydrocarbons at the expense of excessive cracking of the gasoline fraction, which is also a high value product.

Other FCC processes are based on carrying out the cracking reactions at high temperature, such as that disclosed in U.S. Pat. No. 4,980,053, which is incorporated herein by reference. However, this method can result in producing relatively high levels of dry gases.

Still other FCC processes are based on cracking the feed oil at a high temperature with a short contact time and using a catalyst mixture comprising a specific base cracking catalyst and an additive containing a shape-selective zeolite, such as disclosed in U.S. Pat. No. 6,656,346. Processes based on this method are known as High Severity Fluidized Catalytic Cracking (HS-FCC). Operating characteristics of this process include a down-flow reactor, high reaction temperatures, short contact time and high catalyst-to-oil ratio.

Downflow reactors permit higher catalyst-to-oil ratios because the lifting of the solid catalyst particles by vaporized feed as in upflow reactors is not required, and this is particularly suitable for HS-FCC. In addition, HS-FCC processes are operated under considerably higher reaction temperatures, e.g., 550° C. to 650° C. and shorter residence times, e.g., 0.1 to 1.0 seconds as compared to conventional FCC processes. Under these reaction temperatures, two competing cracking reactions occur, thermal cracking and catalytic cracking. Thermal cracking contributes to the formation of coke and of lighter products, such as dry gases, while the catalytic cracking increases propylene and butylenes yields. The short residence time in the downflow reactor also minimizes thermal cracking. Undesirable secondary reactions such as hydrogen transfer reactions which consume olefins are suppressed. The desired short residence time is attained by mixing and dispersing catalyst particles and feed at the reactor inlet followed by immediate separation at the reactor outlet. In order to compensate for the decrease in conversion due to the short contact time, the HS-FCC process is operated at relatively high catalyst-to-oil ratios.

MEROX Process

The mercaptan oxidation process, commonly referred to as the MEROX process, has long been employed for the removal of the generally foul smelling mercaptans found in many hydrocarbon streams and was introduced in the refining industry over fifty years ago. Because of regulatory requirements for the reduction of the sulfur content of fuels for environmental reasons, refineries have been, and continue to be faced with the disposal of large volumes of sulfur-containing by-products.

Disulfide oil (DSO) compounds are produced as a by-product of the MEROX process in which the mercaptans are removed from any of a variety of petroleum streams including liquefied petroleum gas, naphtha, and other hydrocarbon fractions. It is commonly referred to as a 'sweetening process' because it removes the sour or foul smelling mercaptans present in crude petroleum. The term "DSO" is used for convenience in this description and in the claims, and will be understood to include the mixture of disulfide oils produced as by-products of the mercaptan oxidation process.

As noted above, the designation "MEROX" originates from the function of the process itself, i.e., the conversion of mercaptans by oxidation. The MEROX process in all of its applications is based on the ability of an organometallic catalyst in a basic environment, such as a caustic, to accelerate the oxidation of mercaptans to disulfides at near ambient temperatures and pressures. The overall reaction can be expressed as follows:

$$RSH + \tfrac{1}{4}O_2 \rightarrow \tfrac{1}{2}RSSR + \tfrac{1}{2}H_2O \qquad (1)$$

where R is a hydrocarbon chain that may be straight, branched, or cyclic, and the chains can be saturated or unsaturated. In most petroleum fractions, there will be a mixture of mercaptans so that the R can have 1, 2, 3 and up to 10 or more carbon atoms in the chain. This variable chain length is indicated by R and R' in the reaction. The reaction is then written:

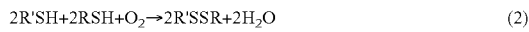

$$2R'SH + 2RSH + O_2 \rightarrow 2R'SSR + 2H_2O \quad (2)$$

This reaction occurs spontaneously whenever any sour mercaptan-bearing distillate is exposed to atmospheric oxygen, but proceeds at a very slow rate. In addition, the catalyzed reaction (1) set forth above requires the presence of an alkali caustic solution, such as aqueous sodium hydroxide. The mercaptan oxidation proceeds at an economically practical rate at moderate refinery downstream temperatures.

The MEROX process can be conducted on both liquid streams and on combined gaseous and liquid streams. In the case of liquid streams, the mercaptans are converted directly to disulfides which remain in the product so that there is no reduction in total sulfur content of the effluent stream.

The MEROX process typically utilizes a fixed bed reactor system for liquid streams and is normally employed with charge stocks having end points above 135° C.-150° C. Mercaptans are converted to disulfides in the fixed bed reactor system over a catalyst, for example, an activated charcoal impregnated with the MEROX reagent, and wetted with caustic solution. Air is injected into the hydrocarbon feedstream ahead of the reactor and in passing through the catalyst-impregnated bed, the mercaptans in the feed are oxidized to disulfides. The disulfides are substantially insoluble in the caustic and remain in the hydrocarbon phase. Post treatment is required to remove undesirable by-products resulting from known side reactions such as the neutralization of $H_2S$, the oxidation of phenolic compounds, entrained caustic, and others.

The vapor pressures of disulfides are relatively low compared to those of mercaptans, so that their presence is much less objectionable from the standpoint of odor; however, they are not environmentally acceptable due to their sulfur content and their disposal can be problematical.

In the case of mixed gas and liquid streams, extraction is applied to both phases of the hydrocarbon streams. The degree of completeness of the mercaptan extraction depends upon the solubility of the mercaptans in the alkaline solution, which is a function of the molecular weight of the individual mercaptans, the extent of the branching of the mercaptan molecules, the concentration of the caustic soda and the temperature of the system. Thereafter, the resulting DSO compounds are separated and the caustic solution is regenerated by oxidation with air in the presence of the catalyst and reused.

Referring to the attached drawings, FIG. 1 is a simplified schematic of a generalized conventional version of a MEROX process of the prior art employing liquid-liquid extraction for removing sulfur compounds in an embodiment in which a combined propane and butane hydrocarbon stream (1) containing mercaptans is treated and which includes the steps of:

introducing the hydrocarbon stream (1) with a homogeneous catalyst into an extraction vessel (5) containing a caustic solution (2), in some embodiments, the catalyst is a homogeneous cobalt-based catalyst;

passing the hydrocarbon catalyst stream in counter-current flow through the extraction section of the extraction vessel (5) in which the extraction section includes one or more liquid-liquid contacting extraction decks or trays (not shown) for the catalyzed reaction with the circulating caustic solution to convert the mercaptans to water soluble alkali metal alkane thiolate compounds;

withdrawing a hydrocarbon product stream (3) that is free or substantially free of mercaptans from the extraction vessel (5);

recovering a combined spent caustic and alkali metal alkane thiolate stream (4) from the extraction vessel (5);

subjecting the spent caustic to catalyzed wet air oxidation in a reactor (10) into which is introduced catalyst (9) and air (6) to provide the regenerated spent caustic (8) and convert the alkali metal alkane thiolate compounds to disulfide oils; and recovering a by-product stream (7) of disulfide oil (DSO) compounds and a minor proportion of other sulfides such as mono-sulfides and tri-sulfides.

The effluents of the wet air oxidation step in the MEROX process preferably comprise a minor proportion of sulfides and a major proportion of disulfide oils. As is known to those skilled in the art, the composition of this effluent stream depends on the effectiveness of the MEROX process, and sulfides are assumed to be carried-over material. A variety of catalysts have been developed for the commercial practice of the process. The efficiency of the MEROX process is also a function of the amount of $H_2S$ present in the stream. It is a common refinery practice to install a prewashing step for $H_2S$ removal.

The disulfide oil compounds produced in the MEROX process can contain various disulfides. For example, a MEROX unit designed for the recovery of propane and butane yields a disulfide oil mixture with the composition set forth in Table 1:

TABLE 1

| Disulfide Oil | W % | BP, ° C. | MW, g/g-mol | Sulfur, W % |
| --- | --- | --- | --- | --- |
| Dimethyldisulfide | 15.7 | 110 | 94 | 68.1 |
| Diethyldisulfide | 33.4 | 152 | 122 | 52.5 |
| Methylethyldisulfide | 49.3 | 121 | 108 | 59.3 |
| Total (Average) | 98.4 | (127) | (109) | (57.5) |

Table 1 indicates the composition of the disulfide oil that is derived from semi-quantitative GC-MS data. No standards were measured against the components; however, the data in Table 1 is accurate as representing relative quantities. Quantitative total sulfur content was determined by energy dispersive x-ray fluorescence spectroscopy which indicated 63 W % of sulfur, and this value will be used in later calculations. The GC-MS results provide evidence of trace quantities of tri-sulfide species; however, the majority of the disulfide oil stream comprises the three components identified in Table 1.

The by-product disulfide oils produced by the MEROX unit can be processed and/or disposed of in various other refinery units' operations. For example, the DSO can be added to the fuel oil pool at the expense of a resulting higher sulfur content of the pool. The DSO can be processed in a hydrotreating/hydrocracking unit at the expense of higher hydrogen consumption. The disulfide oil also has an unpleasant foul or sour smell, which is somewhat less prevalent because of its relatively lower vapor pressure at ambient temperature; however, problems exist in the handling of this oil.

By-product disulfide oil (DSO) compounds from the mercaptan oxidation process can be oxidized, preferably in the presence of a catalyst, and constitute an abundant source of oxidized disulfide oil (ODSO) compounds that are sulfoxides, sulfonates, sulfinates and sulfones. The oxidant can be a liquid peroxide selected from the group consisting of alkyl hydroperoxides, aryl hydroperoxides, dialkyl peroxides, diaryl peroxides, peresters and hydrogen peroxide. The oxidant can also be a gas, including air, oxygen, ozone and oxides of nitrogen. The catalyst is preferably a homogeneous water-soluble compound that is a transition metal containing an active species selected from the group consisting of Mo (VI), W (VI), V (V), Ti (IV), and their combination.

As described in US 2020/0181517, the ODSO compounds have been found to have utility as lubricity additives for diesel fuels that are more economical than currently available additives for that purpose, and as described in US 2020/0181506, the ODSO compounds have also been found to have utility as solvents for aromatic solvent extraction processes, both of which are incorporated herein by reference. In the event that a refiner has produced or has on hand an amount of DSO compounds that is in excess of foreseeable needs for these or other uses, the refiner may wish to dispose of the DSO compounds in order to clear a storage vessel and/or eliminate the product from inventory for tax reasons.

Thus, there is a clear and long-standing need to provide an efficient and economical process for the treatment of the large volumes of DSO by-products and their derivatives to effect and modify their properties in order to facilitate and simplify their environmentally acceptable disposal, and/or to permit the utilization of the modified products within the refinery, and thereby enhance the value of this class of by-products to the refiner.

SUMMARY OF THE INVENTION

The above needs are met and other advantages are provided by the process of the present invention that economically converts disulfide oils and their derivatives, oxidized disulfide oils, which are of relatively low value, to value-added BTX and other aromatics by introducing the DSO compounds as the feed to a fluidized catalytic cracking unit wherein liquid products from the FCC unit are passed to selective naphtha hydrogenation and hydrotreater to produce a hydrotreated naphtha stream containing BTX and other aromatic products. The hydrotreated naphtha stream can be further processed in an aromatics unit including an aromatics extraction zone for the separation of BTX and other heavy aromatics from non-aromatics.

In an embodiment, the present disclosure is directed to an integrated refinery process for the production of BTX from a hydrocarbon feedstream comprising one or more disulfide oils, the process comprising:

a. introducing the hydrocarbon feedstream comprising one or more disulfide oils into a fluidized catalytic cracking (FCC) unit to produce an FCC liquid hydrocarbon products stream, and a cracked gaseous hydrocarbon stream,
   wherein the FCC liquid hydrocarbon products stream comprises diolefins, olefins, sulfur and nitrogen compounds;

b. introducing the FCC liquid hydrocarbon products stream with an effective amount of hydrogen into a selective naphtha hydrogenation and hydrotreating zone to remove all or a substantial portion of diolefins, olefins, sulfur and nitrogen compounds and produce a hydrotreated fluid catalytic cracking naphtha stream containing aromatic products; and c. separating the aromatic products from the hydrotreated fluid catalytic cracking naphtha stream to produce an aromatics stream.

In some embodiments, the separation comprises charging the hydrotreated fluid catalytic cracking naphtha stream to an aromatics unit for separation into a gasoline component raffinate stream, a heavy $C_9+$ aromatics fraction, and the aromatics stream. The aromatics stream can be separated into benzene, xylene and toluene. In some embodiments, all or a portion of the benzene stream, all or a portion of the toluene stream and all or a portion of the heavy C9+ aromatics fraction are directed to a transalkylation zone. The transalkylation zone can operate to produce a transalkylated toluene stream, a transalkylated benzene stream, a transalkylated xylenes stream, a C11+ bottoms stream, and an overhead stream.

The process and apparatus of the present disclosure enables refiners and gas plant operators to convert waste disulfide oils to one or more value-added products. It will be understood that the amount of the disulfide oils introduced into the FCC unit is not critical and that the amount may vary based upon its availability, e.g., as produced by other refinery processes and/or the capacity of storage tanks, and the disulfide oil-containing stream can comprise disulfide oils in the range of 0.1 V % to 100 V %, and in some embodiments, in the range of 0.1 V % to 5 V %, and in other embodiments, in the range of 1 V % to 5 V %.

In the description that follows, the terms "disulfide oil", "DSO", "DSO mixture" and "DSO compounds" may be used interchangeably for convenience.

In the description that follows, the terms "oxidized disulfide oil", "derivative of disulfide oil", "ODSO", "ODSO mixture" and "ODSO compound(s)" may be used interchangeably for convenience.

In the description that follows, the terms "DSO/ODSO", "DSO/ODSO mixture" and "DSO/ODSO compound(s)" may be used interchangeably for convenience.

The phrase "a substantial portion" means at least about 90, 95, 98 or 99 wt % and up to 100 wt %, or the same values of another specified unit.

BRIEF DESCRIPTION OF THE DRAWINGS

The process of the disclosure will be described in more detail below and with reference to the attached drawings in which the same number is used for the same or similar elements, and where:

FIG. 8a-8c are GC-MS spectra of the liquid products of an embodiment of the integrated process of the present disclosure.

DETAILED DESCRIPTION OF PREFERRED EMBODIMENTS

A first embodiment of the process of the present disclosure for treating by-product disulfide oils in an integrated process will be described with reference to FIG. 2.

Figure 1:
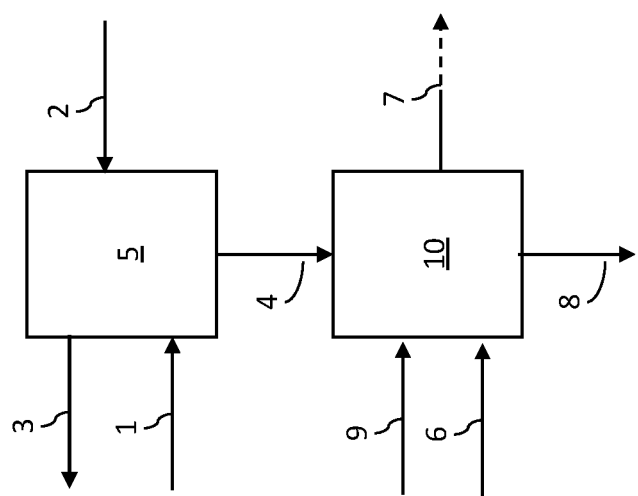
FIG. 1 is a simplified schematic diagram of a generalized version of the mercaptan oxidation or MEROX process of the prior art for the liquid-liquid extraction of a combined propane and butane stream.
Figure 2:
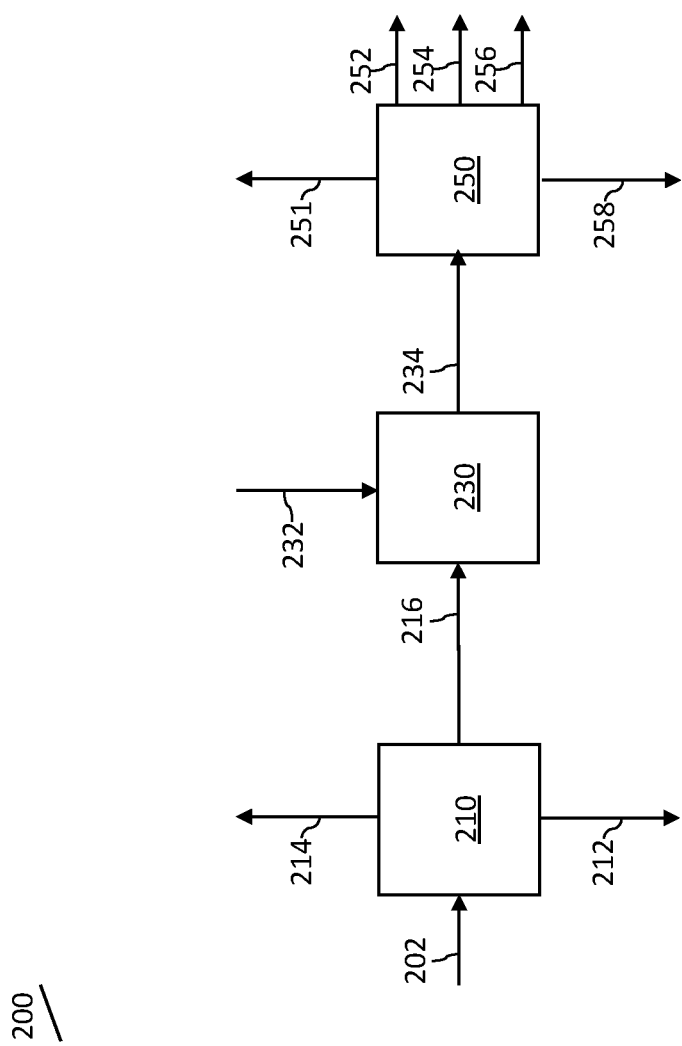
FIG. 2 is a simplified schematic diagram of a first embodiment of the integrated process of the present disclosure.

With reference to FIG. 2, the process and system, includes an FCC unit (210), a selective naphtha hydrogenation and hydrotreating zone (230), and an aromatics unit (250). A DSO stream or a separate ODSO stream, or an appropriately mixed DSO/ODSO stream (202) is introduced into the FCC unit (210) for cracking. Due to their immiscibility, in some embodiments where a mixed DSO/ODSO stream is used, the DSO and ODSO components can be introduced into the FCC unit (210) via separate inlets (not shown). The catalyst (212) is passed from the reaction zone to the regenerator to burn off the coke formed and the cracked liquid hydrocarbon stream (214) is recovered for downstream separation by conventional means known in the art. As is known in the art, the catalyst is typically recycled after regeneration and mixed with fresh catalyst in an amount needed to compensate process losses.

In some embodiments, not shown, some or all of the gas stream (214) from the FCC unit can be sent to downstream refinery processes such as a metathesis unit (not shown).

A cracking liquid hydrocarbon stream (216) from the FCC unit, which is a fluid catalytic cracking naphtha, is further treated in the selective naphtha hydrogenation and hydrotreating zone (230) in the presence of an effective amount of hydrogen obtained from recycle within the selective naphtha hydrogenation and hydrotreating zone (230) and make-up hydrogen (232). In certain embodiments, the amount of hydrogen introduced into the selective naphtha hydrogenation and hydrotreating zone (230) is a predetermined stoichiometric amount.

The selective cracked naphtha hydrogenation and hydrotreating zone (230) operates under conditions effective to ensure removal of substantially all or the complete removal of all diolefins, olefins, sulfur and nitrogen. In some embodiments, full removal of diolefins and olefins is achieved, and sulfur and nitrogen levels are reduced down to less than 0.5 ppmw each, since all contaminants are a limiting contaminant in the aromatics extraction and subsequent processes. In certain embodiments, depending on the composition of the original feedstock, e.g., the DSO and/or ODSO content and the amount and type of co-processed conventional FCC feedstock, typical starting and ending contaminant contents are as follows. If the FCC co-feedstock is straight run VGO (SRVGO), which typically has initial contents of about 25,000 ppmw of sulfur and 700 ppmw of nitrogen, the resulting, reduced-contaminant, FCC gasoline products will typically contain about 1250 ppmw of sulfur and 35 ppmw of nitrogen. If the FCC co-feedstock is hydrotreated VGO, which typically has initial contents of about 800 ppmw of sulfur and 300 ppmw of nitrogen, the resulting, reduced-contaminant, FCC gasoline products will typically contain about 40 ppmw of sulfur and 15 ppmw of nitrogen. These initial sulfur contents are not inclusive of sulfur contributed from the DSO and/or ODSO components, which are easier to crack than sulfur from the co-feedstock. Due to the high temperature conditions effective for sulfur and nitrogen removal in the selective naphtha hydrogenation and hydrotreating zone, saturation of aromatics may occur, for instance, up to about 15% saturation, ahead of recovery. Effluents from the selective naphtha hydrogenation and hydrotreating zone (230) are a hydrotreated fluid catalytic cracking naphtha stream (234), and fuel gas. Effluent fuel gas is recovered and, for instance, passed to a fuel gas system. In certain embodiments ethylbenzene can be recovered (not shown).

The effluent from the selective naphtha hydrogenation and hydrotreating reactor generally contain C5-C9+ hydrocarbons. In certain embodiments, C5-C9+ hydrocarbons are passed to the aromatics unit (250), and the aromatics unit (250) includes a depentanizing step (not shown) to remove C5s. In other embodiments (not shown), the selective cracked naphtha hydrogenation and hydrotreating zone (230) includes a depentanizing step to remove C5s. The hydrotreated fluid catalytic cracking naphtha stream (234), generally containing C6-C9+ hydrocarbons, is passed to the aromatics unit (250).

In certain embodiments, aromatics unit (250) includes operations effective for separation of the aromatic compounds into individual aromatics, such as benzene, toluene, and xylenes in an aromatic recovery complex.

In certain embodiments, aromatics unit (250) includes operations effective for extraction of aromatic compounds from non-aromatic compounds in an aromatics extraction zone and also units for separation of the aromatic compounds into individual aromatics, such as benzene, toluene, and xylenes in an aromatic recovery complex.

A suitable selective naphtha hydrogenation and hydrotreating zone (230) can include, but is not limited to, systems based on technology commercially available from Honeywell UOP, US; Chevron Lummus Global LLC (CLG), US; or Axens, IFP Group Technologies, FR.

The fluid catalytic cracking selective naphtha hydrogenation and hydrotreating zone (230) can contain one or more fixed-bed, ebullated-bed, slurry-bed, moving bed, continuous stirred tank (CSTR) or tubular reactors, in series and/or parallel arrangement. Additional equipment, including exchangers, furnaces, feed pumps, quench pumps, and compressors to feed the reactor(s) and maintain proper operating conditions, are well known and are considered part of the selective naphtha hydrogenation and hydrotreating zone (230). In addition, equipment, including pumps, compressors, high temperature separation vessels, low temperature separation vessels and the like to separate reaction products and provide hydrogen recycle within the selective naphtha hydrogenation and hydrotreating zone (230), are well known and are considered part of the selective naphtha hydrogenation and hydrotreating zone (230).

The aromatics unit (250) operates to separate the hydrotreated fluid catalytic cracking naphtha into high-purity benzene, toluene, and xylenes. As depicted in FIG. 2, a benzene stream (252), a mixed and/or para-xylenes stream (254) and a toluene stream (256) are produced from the aromatics unit (250). Also produced in the aromatics unit (250) are a gasoline component stream (251) containing non-aromatic $C_5/C_6$ compounds, raffinate motor gasoline, in certain embodiments which is substantially free of benzene and a heavier fraction of $C_9+$ aromatics, stream (258), which is not suitable as a gasoline blending component stream In certain embodiments ethylbenzene can be recovered (not shown).

A second embodiment of the process of the present disclosure for treating by-product disulfide oils that includes a transalkylation zone in an integrated process will be described with reference to FIG. 3.

Figure 3:
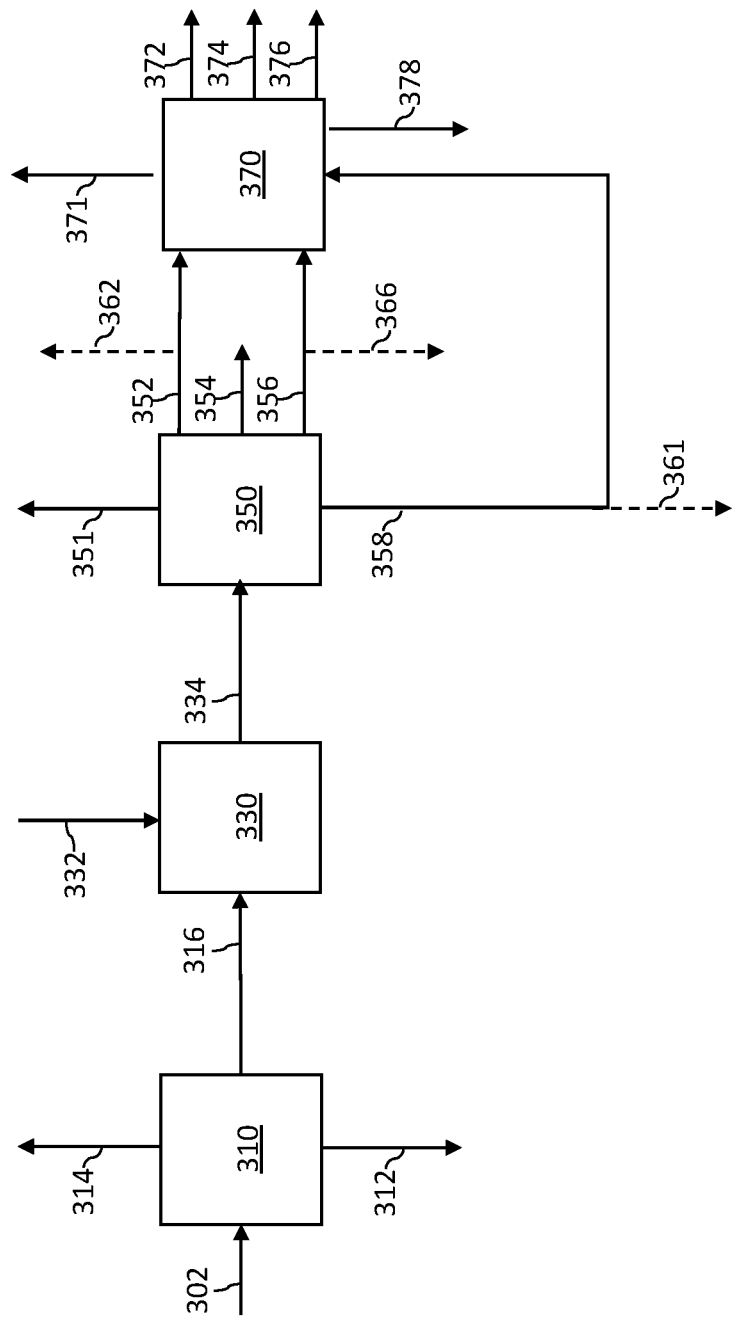
FIG. 3 is a simplified schematic diagram of a second embodiment of the integrated process of the present disclosure.

The embodiment shown in FIG. 3 operates similarly to the embodiment in FIG. 2, with similar references numbers representing similar units/feeds. With reference to FIG. 3, the process and system, includes an FCC unit (310), a selective naphtha hydrogenation and hydrotreating zone (330), an aromatics unit (350), and a transalkylation zone (370).

All or a portion of one or more of toluene stream (356), benzene stream (352), and the heavy fraction of $C_9+$ aromatics (358) from the aromatics unit (350) are passed to transalkylation zone (370). The transalkylation zone (370) operates under conditions effective to produce toluene stream (376), benzene stream (372), xylenes stream (374), a bottoms stream (378) of $C_{11}+$ alkylaromatics ("heavies"), and an overhead stream (371) of light end hydrocarbons ("light-ends gas", generally comprising at least ethane).

In certain embodiments not shown, benzene stream (372) is recovered as a final product or directed back to the transalkylation zone (370) for further reaction with $C_9+$ aromatics (358). In certain embodiments not shown, toluene stream (376) can be either sent for storage, used as a gasoline blending component, or recycled back to the transalkylation zone (370) for further reactions with $C_9+$ aromatics (358). In certain embodiments, not shown, toluene stream (376) can be recycled within the transalkylation zone (370) to extinction. In certain embodiments, not shown, xylenes stream (374) is a para-xylene stream which can be recovered as a final product or recycled back to aromatics unit (350) for eventual para-xylene recovery (not shown).

Depending on desired flow rates and/or extraction tower sizes, one or more of toluene stream (376), benzene stream (372), and xylenes stream (374) can be recycled to aromatics unit (350) for eventual recovery as part of toluene stream (366), benzene stream (362), and xylenes stream (354), respectively. In other embodiments, one or more of toluene stream (376), benzene stream (372), and xylenes stream (374) can be sent for recovery directly with toluene stream (366), benzene stream (362), and xylenes stream (354), respectively.

Product ratio of benzene and xylene in the transalkylation zone (370) can be adjusted by selection of catalyst, feedstock and operating conditions.

A third embodiment of the process of the present disclosure for treating by-product disulfide oils that includes and a source of reformate in an integrated process will be described with reference to FIG. 4.

Figure 4:
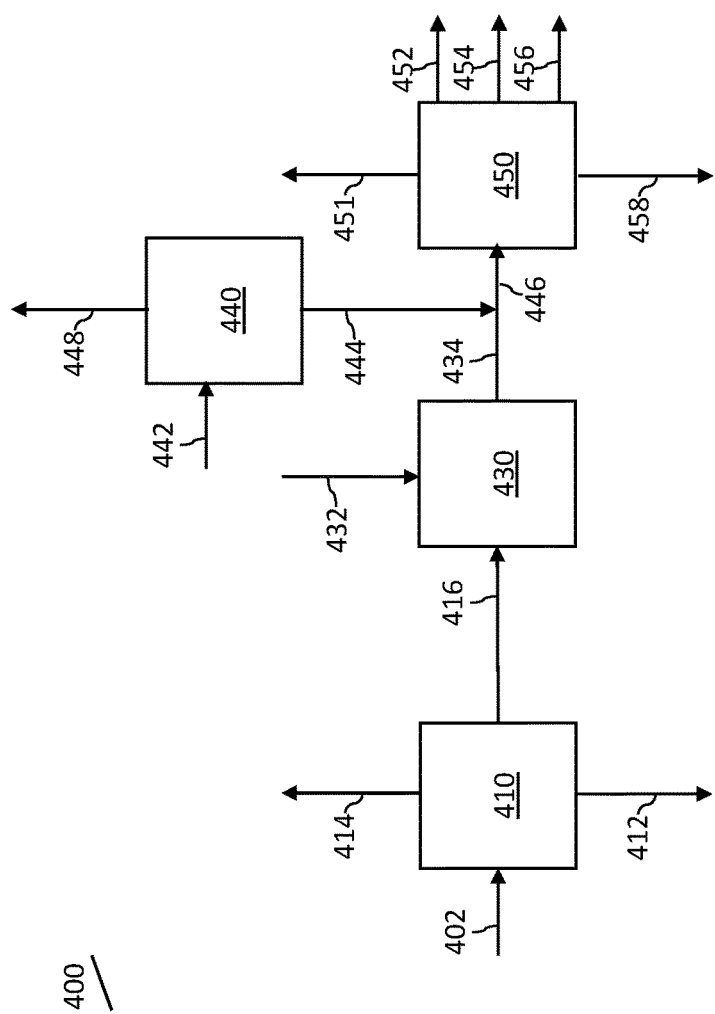
FIG. 4 is a simplified schematic diagram of a third embodiment of the integrated process of the present disclosure.

The embodiment shown in FIG. 4 operates similarly to the embodiment in FIG. 2, with similar references numbers representing similar units/feeds. With reference to FIG. 4, the process and system, includes an FCC unit (410), a selective naphtha hydrogenation and hydrotreating zone (430), catalytic reforming zone (440), and an aromatics unit (450).

A reformer feed (442) is charged to the catalytic reforming zone (440) for treatment and to produce a hydrogen rich gas stream (448), and a reformate stream (444). The reformate stream (444) is mixed with hydrotreated naphtha (434) to produce a mixed naphtha stream (446) which is then sent to aromatics unit (450).

The catalytic reforming zone (440) operates as is known to improve its feed's quality, that is, increase its octane number to produce a reformate stream (444). In addition, the hydrogen rich gas stream (448) is produced, all or a portion of which can optionally be used to meet the hydrogen demand within the integrated system (400).

The reformer feed (442) is typically a hydrotreated heavy naphtha stream, comprising mainly C7-C11 hydrocarbons. A typical composition of the reformer feed (442) is shown in the Table 2 below. In Table 2, the C6 and C12 hydrocarbons are so-called "carried-over" streams from an upstream distillation column due to ineffective separation.

TABLE 2

| Carbon No. | n-Paraffins | Iso-paraffins | Olefins | Naphthenes | Aromatics | Total |
|---|---|---|---|---|---|---|
| C4 | 0.000 | 0.000 | 0.000 | 0.000 | 0.000 | 0.000 |
| C5 | 0.000 | 0.000 | 0.000 | 0.000 | 0.000 | 0.000 |
| C6 | 4.478 | 0.980 | 0.926 | 2.161 | 0.452 | 8.997 |
| C7 | 10.902 | 6.903 | 1.082 | 5.945 | 2.896 | 27.728 |
| C8 | 8.866 | 9.359 | 0.000 | 4.400 | 2.743 | 25.368 |
| C9 | 9.189 | 5.068 | 0.544 | 5.051 | 5.044 | 24.896 |
| C10 | 3.005 | 3.216 | 0.000 | 1.344 | 0.951 | 8.516 |
| C11 | 0.990 | 1.626 | 0.000 | 0.303 | 0.000 | 2.919 |
| C12 | 0.232 | 0.000 | 0.000 | 0.000 | 0.000 | 0.232 |
| Unaccounted | | | | | | 1.344 |
| Total (mass percent) | 37.662 | 27.152 | 2.552 | 19.204 | 12.086 | 100.00 |
| | | | | | Total Oxygenates: | 0.000 |

A fourth embodiment of the process of the present disclosure for treating by-product disulfide oils that includes a transalkylation zone and a source of reformate in an integrated process will be described with reference to FIG. 5.

Figure 5:
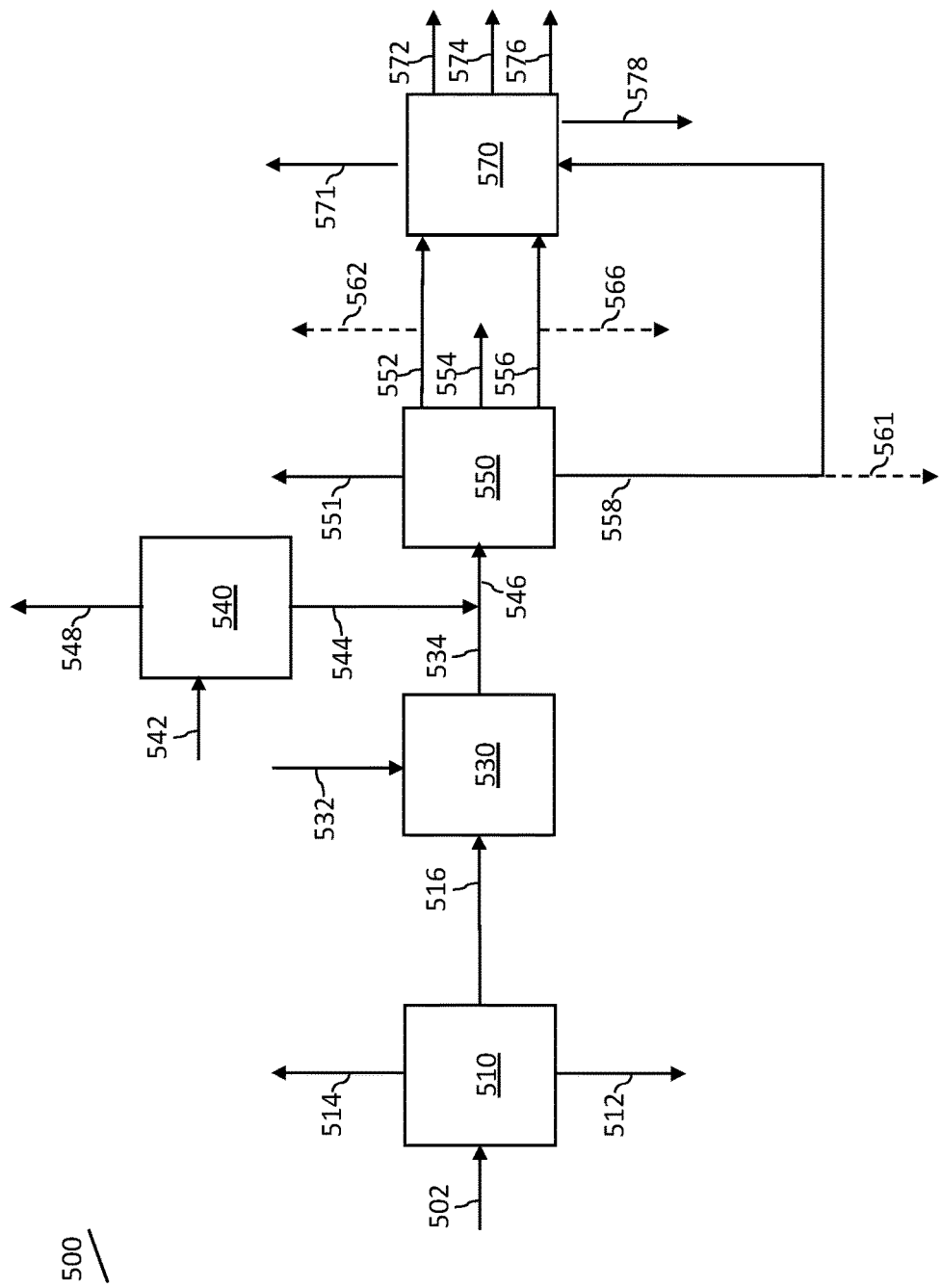
FIG. 5 is a simplified schematic diagram of a fourth embodiment of the integrated process of the present disclosure.

The embodiment shown in FIG. 5 operates similarly to the embodiment in FIG. 3, with similar references numbers representing similar units/feeds. With reference to FIG. 5, the process and system, includes an FCC unit (510), a selective naphtha hydrogenation and hydrotreating zone (530), catalytic reforming zone (540), an aromatics unit (550), and a transalkylation zone (570).

A reformer feed (542) is charged to the catalytic reforming zone (540) for treatment and to produce a hydrogen rich gas stream (548), and a reformate stream (544). The reformate stream (544) is mixed with hydrotreated naphtha (534) to produce a mixed naphtha stream (546) which is then sent to the aromatics unit (550).

The catalytic reforming zone (540) operates as is known to improve its feed's quality, that is, increase its octane number to produce a reformate stream (544). In addition, the hydrogen rich gas stream (548) is produced, all or a portion of which can optionally be used to meet the hydrogen demand within the integrated system (500).

Figure 6:
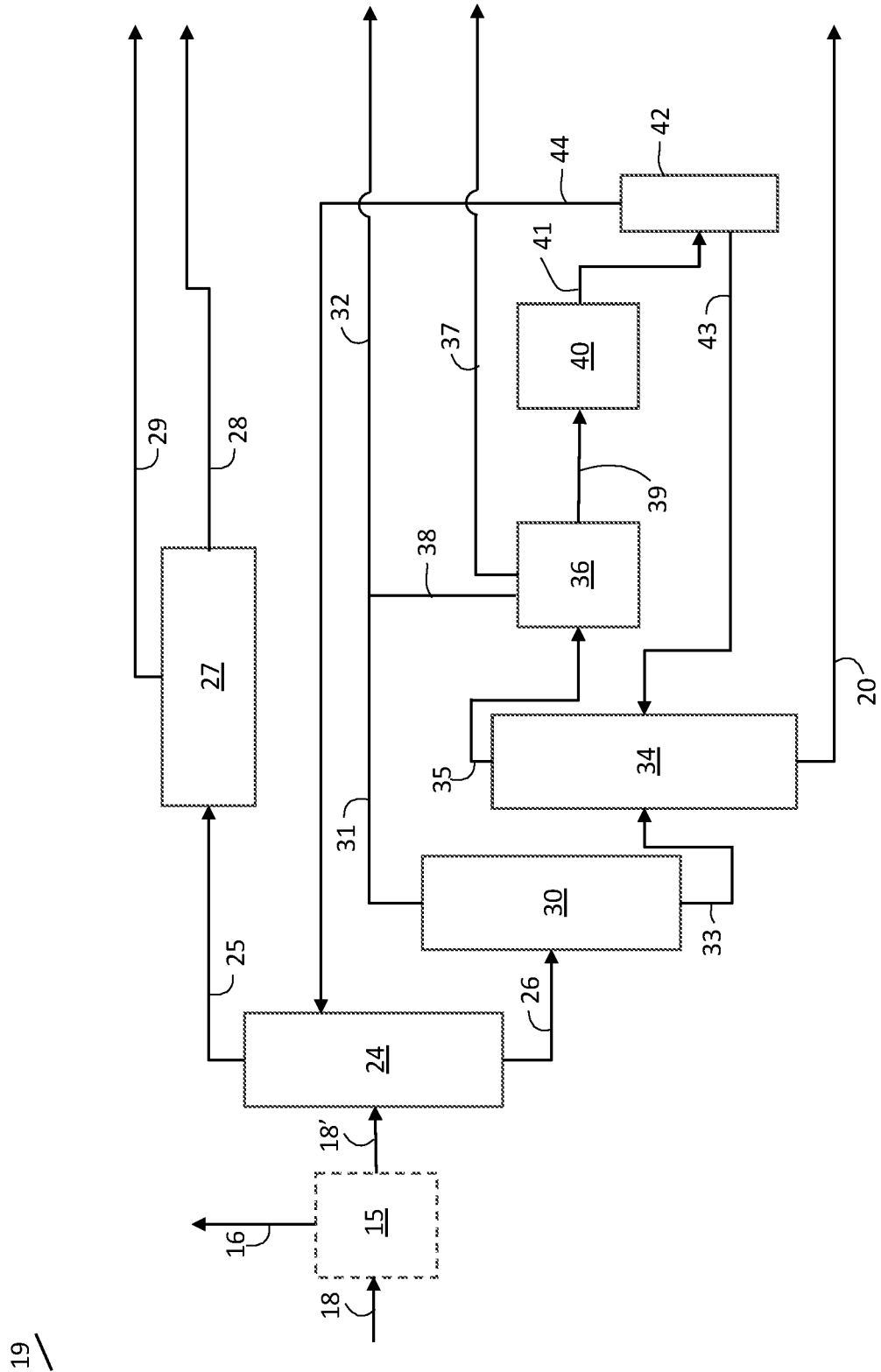
FIG. 6 is a simplified schematic diagram of a conventional aromatics recovery complex.

FIG. 6 is a schematic process flow diagram of a typical aromatic complex (19), corresponding to aromatics unit (250/350/450/550) in FIGS. 2-5. The aromatics feed, (18/18'), is passed to the aromatic complex (19) to extract and separate the aromatic products, such as benzene and mixed xylenes, which have a premium chemical value, and to produce an aromatics and benzene free gasoline blending component. The aromatic complex produces a heavier fraction of C9+ aromatics, stream (20), which is not suitable as a gasoline blending component stream that has stringent specifications.

In the aromatic complex described in conjunction with FIG. 6, toluene may be included in the gasoline cut, but other embodiments are well known in which toluene is separated and/or further processed to produce other desirable products. For instance, toluene along with C9+ hydrocarbon compounds can be subjected to transalkylation to produce ethylbenzene and mixed xylenes, as disclosed in U.S. Pat. No. 6,958,425, which is incorporated herein by reference.

Aromatics feed (18/18') from the hydrotreating zone (230/330/430/530) is divided into a light stream (25) and a heavy stream (26) in a splitter (24). In some embodiments, aromatics feed (18/18') can be hydrotreated naphtha (234/334) or mixed naphtha stream (446/546). The light stream (25), containing C5/C6 hydrocarbons, is sent to a benzene extraction unit (27) to extract a benzene product stream (28) and to recover a gasoline component stream (29) containing non-aromatic C5/C6 compounds, raffinate motor gasoline, in certain embodiments which is substantially free of benzene. Stream (28) corresponds to benzene stream (252/352/452/552) in FIGS. 2-5. Stream (29) corresponds to gasoline component stream (251/351/451/551) in FIGS. 2-5. The heavy stream (26), containing C7+ hydrocarbons, is routed to a heavy splitter (30), to recover a C7 component (31) that forms part of a C7 gasoline product stream (32), and a C8+ hydrocarbon stream (33).

The C8+ hydrocarbon stream (33) is routed to a xylene rerun unit (34), where it is separated into a C8 hydrocarbon stream (35) and a heavier C9+ aromatic hydrocarbon stream (20), for instance which corresponds to the aromatic bottoms stream/C9+ hydrocarbon streams (258/358/458/558) described in FIGS. 2-5. The C8 hydrocarbon stream (35) is routed to a para-xylene extraction unit (36) to recover a para-xylene product stream (37). Stream (37) corresponds to xylenes stream (254/354/454/554) in FIGS. 2-5. Para-xylene extraction unit (36) also produces a C7 cut mogas stream (38), which can be combined with C7 cut mogas stream (31) to produce the C7 cut mogas stream (32), which includes toluene Stream (32) corresponds to toluene stream (256/356/456/556) in FIGS. 2-5. A stream (39) of other xylenes (that is, ortho- and meta-xylenes) is recovered and sent to a xylene isomerization unit (40) to produce additional para-xylene, and an isomerization effluent stream (41) is sent to a splitter column (42). A C8+ hydrocarbon stream (43) is recycled back to the para-xylene extraction unit (36) from the splitter column (42) via the xylene rerun unit (34). Splitter tops, C7− hydrocarbon stream (44), is recycled back to the reformate splitter (24). The heavy fraction (20) from the xylene rerun unit (34) is the aromatic bottoms stream that is conventionally recovered as process reject.

For the embodiments depicted in FIGS. 2 and 3, since the feed to the aromatics unit (19) is selectively hydrogenated upstream in the selective naphtha hydrogenation and hydrotreating zone (230/330), olefins in the feed are hydrogenated. This avoids the need for deolefinization in a clay treating step prior to the para-xylene units of the aromatic recovery complex to remove olefins and diolefins. For the embodiments depicted in FIGS. 4 and 5, i.e., those incorporating a reformer, since the mixed naphtha stream (446/546) would inherently comprise olefins, a clay tower would be needed.

In certain embodiments of operation, the aromatics unit (19) includes an aromatics extraction zone (15) where aromatics (18') are separated from the feed from non-aromatic compounds (16) by extractive distillation using, for instance, n-formylmorpholine (NFM), as an extractive solvent. In these embodiments, it is aromatics stream (18') that is sent to the splitter (24).

Selection of solvent, operating conditions, and the mechanism of contacting the solvent and feed permit control over the level of aromatic extraction. For instance, suitable solvents include n-formylmorpholine, furfural, N-methyl-2-pyrrolidone, dimethylformamide, dimethylsulfoxide, phenol, nitrobenzene, sulfolanes, acetonitrile, or glycols, and can be provided in a solvent to oil ratio of up to about 20:1, in certain embodiments up to about 4:1, and in further embodiments up to about 2:1. Suitable glycols include diethylene glycol, ethylene glycol, triethylene glycol, tetraethylene glycol and dipropylene glycol. The extraction solvent can be a pure glycol or a glycol diluted with from about 2-10 wt % water. Suitable sulfolanes include hydrocarbon-substituted sulfolanes (e.g., 3-methyl sulfolane), hydroxy sulfolanes (e.g., 3-sulfolanol and 3-methyl-4-sulfolanol), sulfolanyl ethers (e.g., methyl-3-sulfolanyl ether), and sulfolanyl esters (e.g., 3-sulfolanyl acetate).

The aromatic extraction zone (15) can operate at a temperature in the range of from about 40-200, 40-150, 60-200, 60-150, 86-200 or 80-150° C. The operating pressure of the aromatic separation apparatus can be in the range of from about 1-20, 1-16, 3-20, 3-16, 5-20 or 5-16 barg. Types of apparatus useful as the aromatic extraction zone in certain embodiments of the system and process described herein include extractive distillation columns.

Figure 7:
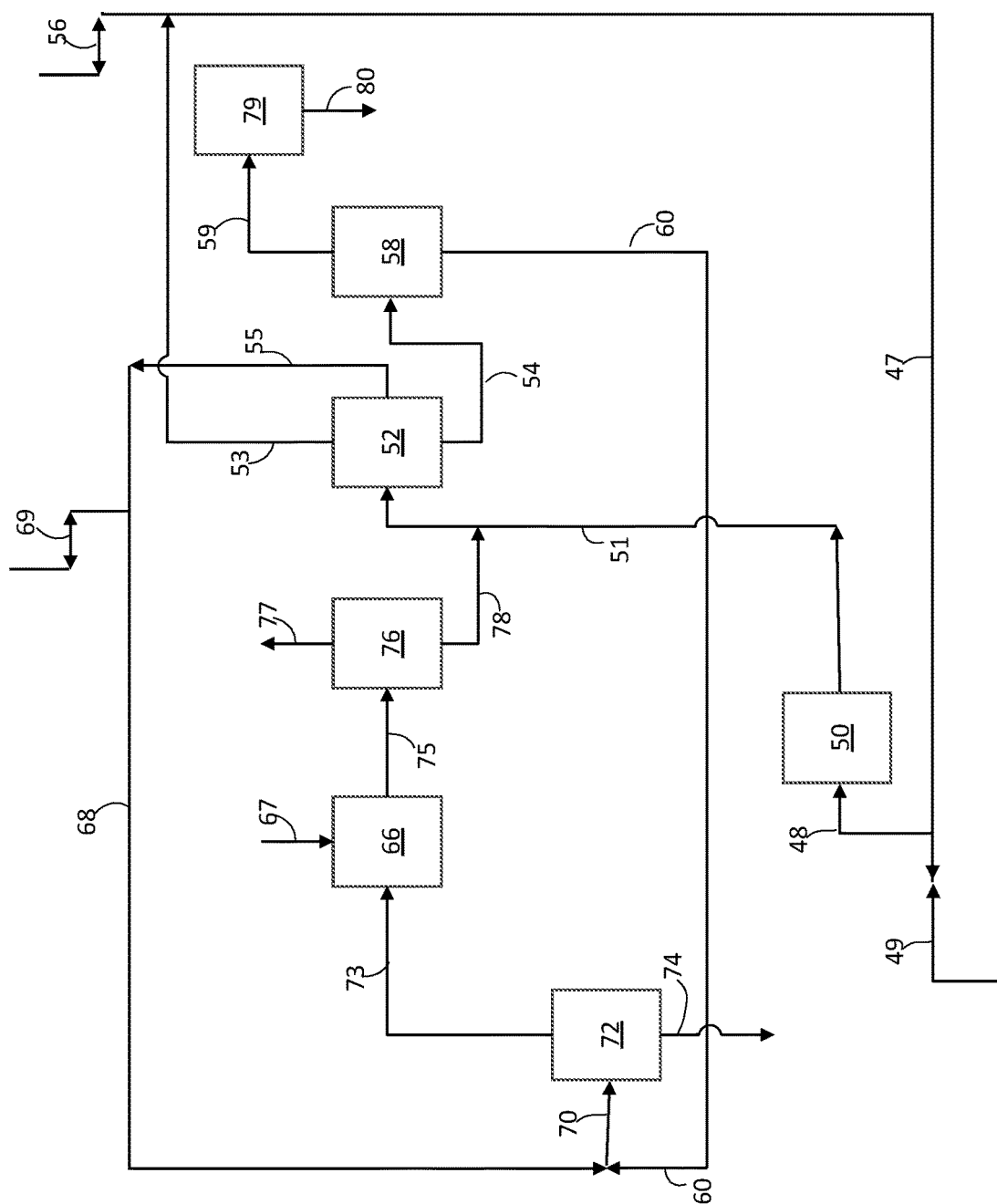
FIG. 7 is a simplified schematic diagram of a conventional system for aromatic transalkylation.

FIG. 7 is a schematic process flow diagram of a transalkylation/toluene disproportionation zone for aromatic transalkylation of C9+ aromatics into C8 aromatics ethylbenzene and xylenes, for instance similar to that disclosed in U.S. Pat. No. 6,958,425. In general, the units of the transalkylation/toluene disproportionation zone operate under conditions and in the presence of catalyst(s) effective to disproportionate toluene and C9+ aromatics. Benzene and/or toluene can be supplied from the integrated system and processed herein or externally as needed. While an example of a transalkylation/toluene disproportionation zone is show in FIG. 7, it is understood that other processes can be used and integrated within the system and process herein for catalytic conversion of aromatic complex bottoms.

A C9+ alkylaromatics feedstream (49) for transalkylation can be all or a portion of stream (20) from the aromatic complex (for instance from the xylene rerun unit) in FIG. 6. In the process, a C9+ alkylaromatics stream (49) is admixed with a benzene stream (47) to form a combined stream (48) as the feed to a first transalkylation reactor (50) (optionally also including an additional hydrogen stream). After contact with a suitable transalkylation catalyst such as a zeolite material, a first transalkylation effluent stream (51) is produced and passed to a first separation column (52). The separation column (52), which also receives a second transalkylation effluent stream (78), separates the combined stream into an overhead benzene stream (53); a C8+ aromatics bottoms stream (54) including ethylbenzene and xylenes; and a side-cut toluene stream (55). The overhead benzene stream (53) is recycled back to the transalkylation reactor (50) via stream (47) after benzene is removed or added, shown as stream (56). In certain embodiments, added benzene can be all or a portion of benzene stream (28) from the aromatic complex in FIG. (6). In certain embodiments, removed benzene corresponds to benzene stream (372/572) in FIGS. 3 and 5. The C8+ aromatics bottoms stream (54) is passed to a second separation column (58) from which an overhead stream (59) containing ethylbenzene and mixed xylenes is directed to a para-xylene production unit (79) to produce a para-xylene stream (80). Stream (80) corresponds to xylenes stream (374/574) in FIGS. 3 and 5. In certain embodiments the para-xylene production unit (79) can operate similar to the para-xylene extraction unit (36), the xylene isomerization unit (40), or both the para-xylene extraction unit (36) and the xylene isomerization unit (40). In further embodiments the para-xylene production unit (79) can be the para-xylene extraction unit (36), the xylene isomerization unit (40), or both the para-xylene extraction unit (36) and the xylene isomerization unit (40). In embodiments where the para-xylene production unit (79) includes both a para-xylene extraction unit and a xylene isomerization unit, stream (80) is a para-xylene stream and a para-xylene-lean stream will be internally recycled (not shown) to the xylene isomerization unit within the para-xylene production unit (79) to produce more para-xylene compounds.

A bottoms C9+ alkylaromatics stream (60) is withdrawn from the second separation column (58). The side-cut toluene stream (55) is ultimately passed to a second transalkylation unit (66) via stream (68) after toluene is added or removed, shown as stream (69). In certain embodiments added toluene includes all or a portion of the C7 streams (31) or (38), or the combined stream (32), from the aromatic complex in FIG. 6. In certain embodiments, removed toluene corresponds to toluene stream (376/576) in FIGS. 3 and 5. The toluene stream (68) is admixed with the bottoms C9+ alkylaromatics stream (60) to form a combined stream (70) that enters a third separation column (72). The separation column (72) separates the combined stream (70) into a bottoms stream (74) of C11+ alkylaromatics ("heavies"), and an overhead stream (73) of C9, C10 alkylaromatics, and lighter compounds (including C7 alkylaromatics). In certain embodiments, bottoms stream (74) corresponds to bottoms stream (378/578) in FIGS. 3 and 5. The overhead stream (73) is directed to a second transalkylation unit (66), along with a hydrogen stream (67). After contact with a transalkylation catalyst, a second transalkylation effluent stream (75) is directed to a stabilizer column (76) from which an overhead stream (77) of light end hydrocarbons ("light-ends gas", generally comprising at least ethane) is recovered, and a bottom stream (78) of the second transalkylation product is directed to the first separation column (52). In certain embodiments, overhead stream (77) corresponds to overhead stream (371/571) in FIGS. 3 and 5. Since it is a fuel oil quality stream, all, a major portion, a significant portion or a substantial portion of the bottoms stream (74) of C11+ alkylaromatics can be passed to a fuel oil pool. In some embodiments, all or a portion of the bottoms stream (74) of C11+ alkylaromatics can be passed to a hydrodearylation process downstream (not shown).

The bottoms fraction (20) from the aromatic complex (19) can be subjected to additional processing steps, and in certain embodiments separation and processing steps, to recover additional aromatic products and/or gasoline blending material. For instance, all or a portion of the C9+ heavy fraction (20) from the xylene re-run unit (34) can be converted. In additional embodiments in which transalkylation is incorporated, all or a portion of a bottoms stream (74) of C11+ alkylaromatics from the separation column (72) can be processed to recover additional aromatic products and/or gasoline blending material. While FIG. 6, and optionally FIG. 6 in combination with FIG. 7, show embodiments of conventional systems and processes for separation of aromatic products and gasoline products, C9+ heavy fractions derived from other separation processes can be suitable as feeds in the systems and processes described herein, for instance, pyrolysis gasoline from steam cracking having condensed aromatics such as naphthalenes.

The selective naphtha hydrogenation and hydrotreating zone (230/330/430/530) is operated under conditions effective to treat fluid catalytic cracking naphtha to produce hydrotreated naphtha (234/334/434/534) that can be used as feed to the aromatics unit (250/350/450/550) for recovery of BTX streams.

In certain embodiments, the selective naphtha hydrogenation and hydrotreating zone (230) operating conditions include:

a reactor temperature (° C.) in the range of from about 150-430, 300-430, 320-430, 340-430, 150-420, 300-420, 320-420, 340-420, 150-400, 300-400, 320-400, 340-400, 150-380, 300-380, 320-380, 340-360, 150-360, 300-360, 320-360 or 340-360;

a hydrogen partial pressure (barg) in the range of from about 10-80, 10-60, 10-40, 20-80, 20-40, 20-60, 35-80, 35-60 or 35-40;

a hydrogen gas feed rate (standard liters per liter of hydrocarbon feed, SLt/Lt) of up to about 1000, 700 or 500, in certain embodiments from about 100-1000, 100-700, 100-500, 200-1000, 200-700, 200-500, 300-1000, 300-700 or 300-500; and a liquid hourly space velocity ($h^{-1}$), on a fresh feed basis relative to the hydrotreating catalysts, in the range of from about 0.1-10.0, 0.1-6.0, 0.1-5.0, 0.1-4.0, 0.1-2.0, 0.5-10.0, 0.5-5.0, 0.5-2.0, 0.8-10.0, 0.8-6.0, 0.8-5.0, 0.8-4.0, 0.8-2.0, 1.0-10.0, 1.0-6.0, 1.0-5.0, 1.0-4.0 or 1.0-2.0.

An effective quantity of hydrotreating catalyst is provided in the selective naphtha hydrogenation and hydrotreating zone (230/330/430/530), including those possessing hydrotreating functionality and which generally contain one or more active metal component of metals or metal compounds (oxides or sulfides) selected from the Periodic Table of the Elements IUPAC Groups 6-10. In certain embodiments, the active metal component is one or more of Co, Ni, W and Mo. The active metal component is typically deposited or otherwise incorporated on a support, such as amorphous alumina, amorphous silica alumina, zeolites, or combinations thereof. In certain embodiments, the catalyst used in the selective naphtha hydrogenation and hydrotreating zone (230) includes one or more catalyst selected from Co/Mo, Ni/Mo, Ni/W, and Co/Ni/Mo. Combinations of one or more of Co/Mo, Ni/Mo, Ni/W and Co/Ni/Mo, can also be used. The combinations can be composed of different particles containing a single active metal species, or particles containing multiple active species. In certain embodiments, a Co/Mo hydrodesulfurization catalyst is suitable.

The FCC unit can operate as either a riser or a downer. The operation conditions for a suitable riser FCC unit include:

a reaction temperature (° C.) of from about 480-650, 480-620, 480-600, 500-650, 500-620, or 500-600;

a reaction pressure (barg) of from about 1-20, 1-10, or 1-3;

a contact time (in the reactor, seconds) of from about 0.5-10, 0.5-5, 0.5-2, 1-10, 1-5, or 1-2; and a catalyst-to-feed ratio of about 1:1 to 15:1, 1:1 to 10:1, 1:1 to 20:1, 8:1 to 20:1, 8:1 to 15:1, or 8:1 to 10:1.

The operating conditions for a suitable downflow FCC unit include:

a reaction temperature (° C.) of from about 550-650, 550-630, 550-620, 580-650, 580-630, 580-620, 590-650, 590-630, 590-620;

a reaction pressure (barg) of from about 1-20, 1-10, or 1-3;

a contact time (in the reactor, seconds) of from about 0.1-30, 0.1-10, 0.1-0.7, 0.2-30, 0.2-10, or 0.2-0.7; and a catalyst-to-feed ratio of about 1:1 to 40:1, 1:1 to 30:1, 10:1 to 30:1, or 10:1 to 30:1.

The DSO feed, ODSO feed or mixed DSO/ODSO feedstream can be processed together with other conventional FCC feedstocks including, but not limited to vacuum gas oils, for example boiling in the range of from 350° C. to 565° C., deasphalted oils from a solvent deasphalting unit, for example boiling above 520° C., delayed coker gas oils, for example boiling in the range similar to vacuum gas oils, for instance up to about 565° C., hydrocracker bottoms, or atmospheric residues, for example boiling above 350° C.

The DSO feed, ODSO feed or mixed DSO/ODSO feedstream can comprise an amount in the range of from 0.1 V % to 100 V % of the initial feedstock, and in other embodiments, in the range of from 0.1 V % to 5 V %, and in even other embodiments, in the range of from 1 V % to 5 V %. The FCC unit can have a pretreatment unit, i.e., a VGO hydrotreater operating with a hydrogen partial pressure in the range of from 30 bar to 70 bar, or more preferably in the range of from 50 bar to 70 bar upstream of the FCC unit to improve the quality of the feedstock.

EXAMPLE

A disulfide oil sample, the properties and composition of which are provided in Table 1, was subjected to a fluidized catalytic cracking process using a Micro Activity Test (MAT) unit. The MAT runs were conducted in a fixed-bed reactor according to ASTM D51549 entitled "Determining Activity and Selectivity of FCC Catalysts by Microactivity Test". A proprietary FCC catalyst based on USY zeolite was used for the tests. The catalyst comprises a zeolite as an active component and clay as filler, both having microporosity and alumina, and silica as binders having mesoporosity, The catalyst was conditioned according to ASTM D4463 entitled "Metals-Free Steam Deactivation of Fresh Fluid Cracking Catalyst". According to this method, the catalyst used was aged at 810° C. and ambient pressure, i.e., at 1 bar, under a flow of 100% steam for 6 hours. An FCC MAT test was conducted at catalyst-to-oil (C/O) ratios of 3.26 and under conventional FCC conditions, i.e., 530° C. Table 3 indicates the product yields.

TABLE 3

| | |
|---|---|
| Temperature ° C. | 530 |
| Catalyst/Oil Ratio, W %/W % | 3.26 |
| Yields, W % | |
| Total Gas | 31.31 |
| Total Liquid Products | 60.89 |
| Coke | 7.80 |
| Total | 100.0 |

As indicated by the data in Table 3, at 530° C. and a catalyst-to-oil ratio of 3.26, the fluidized catalytic cracking of the DSO sample yielded 60.89 W % of liquid products.

The liquid products from Example 1 were analyzed by GC-MS and the results are shown in FIG. 8a-c. A GC equipped with a mass spectrometer detector (MSD) was used for the analysis of the organic sulfur in the samples. A non-polar column (methyl siloxane, 0×0.25×0.25) operated in constant flow mode was used. The GC oven was operated at a temperature in the range of from 50° C. to 320° C. at a temperature gradient of 10° C./min and was kept there for 20 minutes. The MSD was operated in a full scan mode. Samples were diluted in toluene (1:1, wt/wt) prior to injection in the GC-MS. The identification of the compounds was achieved by comparing the acquired mass spectra with those present in a library (NIST). FIG. 8a shows the GC-MS spectrum for the DSO sample at a retention time of 12-30 minutes. FIG. 8b shows the GC-MS spectrum for the DSO sample at a retention time of 20-60 minutes. FIG. 8c shows the GC-MS spectrum for the DSO sample at a retention time of 60-140 minutes. The GC-MS spectra of the liquid FCC products indicate that BTX is formed.

It will be understood from the above description that the process of the present disclosure provides a cost effective and environmentally acceptable means for disposing of by-product disulfide oils, and can convert what may be essentially a low value refinery material into commercially important commodity products.

The process of the present invention has been described above and in the attached figures; process modifications and variations will be apparent to those of ordinary skill in the art from this description and the scope of protection is to be determined by the claims that follow.

The invention claimed is:

1. A process for the production of BTX from a hydrocarbon feedstream comprising one or more disulfide oils, the process comprising:
   a. introducing the hydrocarbon feedstream comprising one or more disulfide oils into a fluidized catalytic cracking (FCC) unit to produce an FCC liquid hydrocarbon products stream, and a cracked gaseous hydrocarbon stream,
      wherein the FCC liquid hydrocarbon products stream comprises diolefins, olefins, sulfur and nitrogen compounds;
   b. introducing the FCC liquid hydrocarbon products stream with an effective amount of hydrogen into a selective naphtha hydrogenation and hydrotreating zone to remove all or a substantial portion of diolefins, olefins, sulfur and nitrogen compounds and produce a selective naphtha hydrogenation and hydrotreating product stream containing aromatic products; and
   c. separating the aromatic products from the selective naphtha hydrogenation and hydrotreating product stream to produce an aromatics stream.

2. The process of claim 1 in which the separation in step (c) comprises charging the selective naphtha hydrogenation and hydrotreating product stream to an aromatics unit for separation into a gasoline component raffinate stream, a heavy $C_9$+ aromatics fraction, and the aromatics stream.

3. The process as in claim 2 in which the aromatics stream is separated into benzene, xylene and toluene.

4. The process as in claim 3 in which the benzene, xylene and toluene are recovered as separate streams.

5. The process of claim 3 wherein all or a portion of the separated benzene, all or a portion of the separated toluene and all or a portion of the separated heavy $C_9$+ aromatics fraction are directed to a transalkylation zone.

6. The process of claim 5 in which the transalkylation zone produces a transalkylated toluene stream, a transalkylated benzene stream, a transalkylated xylenes stream, a $C_{11}+$ bottoms stream, and an overhead stream.

7. The process of claim 6 in which the transalkylated toluene stream, the transalkylated benzene stream, the transalkylated xylene stream are recovered as separate streams.

8. The process of claim 1, in which the selective naphtha hydrogenation and hydrotreating product stream is mixed with a reformate stream to produce a mixed naphtha stream from which the aromatic products are separated.

9. The process of claim 1, in which the FCC liquids hydrocarbon products stream comprises BTX.

10. The process of claim 1, in which the amount of sulfur in the FCC liquid hydrocarbon products stream is reduced in the selective naphtha hydrogenation and hydrotreating zone to less than 0.5 ppmw.

11. The process of claim 1, wherein the hydrocarbon feedstream comprising one or more disulfide oils comprises disulfide oil compounds and oxidized disulfide oil compounds.

12. The process of claim 11, wherein the hydrocarbon feedstream comprising one or more disulfide oils comprises disulfide oils present in an effluent refinery hydrocarbon stream recovered downstream of a MEROX process, and wherein the oxidized disulfide oil compounds are catalytically oxidized disulfide oils present in an effluent refinery hydrocarbon stream recovered downstream of a MEROX process.

13. The process of claim 1, wherein the hydrocarbon feedstream comprising one or more disulfide oils comprises one or more disulfide compounds.

14. The process of claim 1, wherein the hydrocarbon feedstream comprising one or more disulfide oils is mixed with one or more conventional FCC unit hydrocarbon feedstocks.

15. The process of claim 1, wherein the hydrocarbon feedstream comprising one or more disulfide oils is mixed with a vacuum gas oil stream or atmospheric residue stream.

16. The process of claim 1, wherein disulfide oils are present in the hydrocarbon feedstream comprising one or more disulfide oils in the range of from 0.1 V % to 5 V %.

\* \* \* \* \*